(12) United States Patent
Boussignac

(10) Patent No.: US 6,516,801 B2
(45) Date of Patent: *Feb. 11, 2003

(54) DEVICE FOR RESPIRATORY ASSISTANCE

(76) Inventor: Georges Boussignac, 1, Avenue de Provence, 92160 Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/349,121

(22) Filed: Jul. 8, 1999

(65) Prior Publication Data

US 2001/0042548 A1 Nov. 22, 2001

(30) Foreign Application Priority Data

Aug. 5, 1998 (FR) .............................. 98 10044

(51) Int. Cl.⁷ .............................................. A61M 16/00
(52) U.S. Cl. ............................. 128/204.24; 128/204.18
(58) Field of Search ...................... 128/204.22, 204.23, 128/205.23, 202.22, 202.27, 207.16, 200.12, 204.25, 203.23, 912, 203.16, 203.15, 203.18, 204.24

(56) References Cited

U.S. PATENT DOCUMENTS

| | | | | |
|---|---|---|---|---|
| 3,881,480 A | * | 5/1975 | Lafourcade | 128/145.8 |
| 4,207,884 A | * | 6/1980 | Isaacson | 128/200.24 |
| 4,558,708 A | * | 12/1985 | Labuda et al. | 128/719 |
| 4,592,349 A | * | 6/1986 | Bird | 128/204.25 |
| 5,036,847 A | * | 8/1991 | Boussignac et al. | 128/207.14 |
| 5,474,060 A | * | 12/1995 | Evans | 128/204.22 |
| 5,642,726 A | * | 7/1997 | Owens et al. | 128/200.26 |
| 5,715,815 A | * | 2/1998 | Lorensen et al. | 128/207.14 |
| 5,720,282 A | * | 2/1998 | Wright | 128/207.14 |

* cited by examiner

Primary Examiner—Dennis Ruhl
Assistant Examiner—Mital Patel
(74) Attorney, Agent, or Firm—Fisher, Christen & Sabol

(57) ABSTRACT

A device for respiratory assistance which comprises a tube (4) having at least one auxiliary channel (8) connected to a source of respirable gas (25). The conduit (28) connects the source of respirable gas (25) to the auxiliary channel (8). The device further includes:

toward the source (25), a device for loss of head (30) which is able to impose on the jet of respirable gas a predetermined flow rate value and a predetermined pressure value; and toward said auxiliary channel (8), a calibrated exhaust valve (32) which is able to bring the conduit (28) into communication with the atmosphere when the pressure in the conduit (28) exceeds said predetermined pressure value.

3 Claims, 2 Drawing Sheets

DEVICE FOR RESPIRATORY ASSISTANCE

The subject of the present invention is a device for respiratory assistance which can be used on patients in whom spontaneous respiration is absent or inadequate, whether or not said patients are placed under artificial respiration.

Various devices are known, such as masks and oral, nasal, endotracheal and tracheotomy probes or cannulas, which are intended to form the junction between an artificial respiration and/or anesthesia apparatus and the respiratory tract of a patient. These devices, essentially in the form of tubes, can, depending on the circumstances, include immobilizing means such as flanges or collars in the vicinity of the proximal end for holding them on the mouth or nose of the patient, or inflatable balloons in the vicinity of the distal end for holding them by friction in the trachea.

The known devices have important disadvantages. Thus, for example, when a tube of a known type is disconnected from the artificial respirator and the patient needs oxygen-enriched air, it is necessary to introduce into said tube a probe which is connected to an oxygen source. Moreover, in cases of inadequate spontaneous respiration, the patient must necessarily remain connected to the respirator until spontaneous respiration has been completely re-established.

To overcome these disadvantages, it has already been proposed, for example in documents EP-A-0 390 684 and EP-A-0 701 834, to provide devices for respiratory assistance which, in addition to the main channel formed by the tube, comprise at least one auxiliary channel, for example formed in the wall of said tube, permitting injection of a jet of respirable gas (oxygen, air or air/oxygen mixture) intended to ventilate the patient, this auxiliary channel opening into the main channel in the vicinity of the distal end of the latter.

Of course, these latter known devices for respiratory assistance include safety means which are able to stop the functioning of the device in the event of overpressure in the respiratory tract of the patient and/or in said tube.

The object of the present invention is to improve said devices for respiratory assistance in order to increase the safety of their use still further.

To this end, according to the invention, the device for respiratory assistance comprising a tube which forms a main channel and which is intended to be connected via its distal end to the respiratory tract of a patient so that said main channel connects the respiratory system of said patient to the outside, said device moreover comprising at least one auxiliary channel connected to a source of respirable gas so as to permit the insufflation of a jet of such a respirable gas into said respiratory system, and opening into said main channel in the vicinity of the distal end of the latter, is distinguished by the fact that, in the conduit connecting said source of respirable gas to said auxiliary channel, it includes:

toward said source, a device for loss of head which is able to limit the flow rate and the pressure of said respirable gas available at the outlet of said source, and to impose on said jet of respirable gas a predetermined flow rate value and a predetermined pressure value; and toward said auxiliary channel, a calibrated exhaust valve which is able to bring said conduit into communication with the atmosphere when the pressure in said conduit exceeds said predetermined pressure value.

Thus, by virtue of the present invention, the safety system acts at the level of the injection of the jet of respirable gas and advantageously complements the safety systems of the known devices mentioned above which safety systems act at the level of the patient's airways.

It should be noted that in order to obtain the maximum level of safety sought by the present invention, the combination of the device for loss of head and the calibrated exhaust valve is indispensable. This is because the device for loss of head lowers the flow rate and pressure of the jet of respirable gas so that, when this pressure exceeds said predetermined value, the exhaust valve is able to evacuate the entire jet of respirable gas into the atmosphere. If said device for loss of head were to be omitted, the flow rate and the pressure of the jet of respirable gas would be able to reach values such that said jet would be able at least in part to pass through said calibrated exhaust valve in the direction of the patient's airways, instead of being evacuated into the atmosphere. This could then result in serious injury to the patient.

Such a device for loss of head can be of any known type, such as needle screw restrictions, channels of small internal diameter, etc., and the same applies to said calibrated exhaust valve, which can be of the type with plunger and pierced cylinder, with a ball or flap charged by a spring, etc.

Said device for loss of head is preferably adjustable in such a way as to make it possible to impose on said jet of respirable gas a plurality of predetermined flow rate values and pressure values. Likewise, it is advantageous for the calibration of said exhaust valve to be adjustable. Thus, it is possible to adapt the device according to the present invention to the particular case of each patient.

Especially in the case where at least part of the conduit connecting the source of respirable gas to the auxiliary channel is incorporated in said tube, the device for loss of head and/or said calibrated exhaust valve could also be incorporated in said tube. However, they are preferably external to it.

By virtue of the device for loss of head, it is particularly easy to provide a humidifier in said conduit connecting the source of respirable gas to the auxiliary channel. This is because this device for loss of head makes it possible to lower the pressure of the jet of respirable gas to a level permitting good humidification thereof. It is thereby possible to prevent the patient's mucous membrane from drying out. Said humidifier is preferably arranged between the device for loss of head and the calibrated exhaust valve.

Moreover, in order to prevent the jet of humidified respirable gas from directly hitting the mucous membrane, and the risk of its kinetic energy causing trauma to said mucous membrane, it is advantageous if, as is described in European Patent EP-A-0 390 684, at least the distal end of said auxiliary channel opening into the main channel is parallel to the latter and if there are provided, opposite the distal orifice of said auxiliary channel, means for deflecting said jet of respirable ventilation gas toward the inside of said main channel.

Thus, the jet of humidified respirable gas, under low pressure, passing through said auxiliary channel, is deflected toward the axis of the main channel when it penetrates into the latter. Downstream of said deflection means, that is to say inside the main channel, the pressure of said jet of respirable gas falls and the jet emerges at even lower pressure via the distal orifice of the tube. Experience has shown that downstream of the distal outlet of the tube, the pressure is low and is maintained constant throughout the respiratory space. This pressure is dependent on the flow rate of respirable gas in the auxiliary channels. Consequently, with the device for respiratory assistance according to the invention, it is possible, for example, to supply humid oxygen or a humid mixture of air and oxygen directly to the lungs, at the level of the carina, and thereby to suppress the dead space which exists in the current probes and which is about one third of the total respiratory volume of adults and about half the total respiratory volume of premature babies.

The suppression of this dead space corresponds to an increase in performance of the respiratory cycle of more than 25% in all patients and of nearly 50% in certain cases.

When the device according to the invention comprises a plurality of auxiliary channels, it is advantageous for at least some of them to be supplied jointly with respirable gas. Such joint supply of said channels can be achieved by way of a distribution ring which is coaxial with said tube. Moreover, said auxiliary channels which are not jointly supplied can be used for introducing additional gaseous products such as medicinal products.

Thus, it will be seen that the device according to the invention permits, in complete safety:

humidification of the insufflated respirable gas, long-term intubation of the respiratory assistance device without drying, injection of medicines or anesthetics during respiratory assistance, dynamic measurement of pressures, since it suffices to provide auxiliary channels to which appropriate probes are associated, establishment of a microflow of respirable gas in the auxiliary channels to prevent obstruction of said channels by mucus, an increase in the volume exchanged, since the pressure is automatically limited and there is no risk of crushing of the pulmonary capillaries, for the same quantity of oxygen exchanged, a decrease in the amount of oxygen in the mixture, which reduces the secondary effects of the assistance, the possibility of using respirators which are less expensive then the current respirators.

The figures in the attached drawing will show clearly how the invention can be achieved. In these figures, identical references designate like elements.

Figure 1:
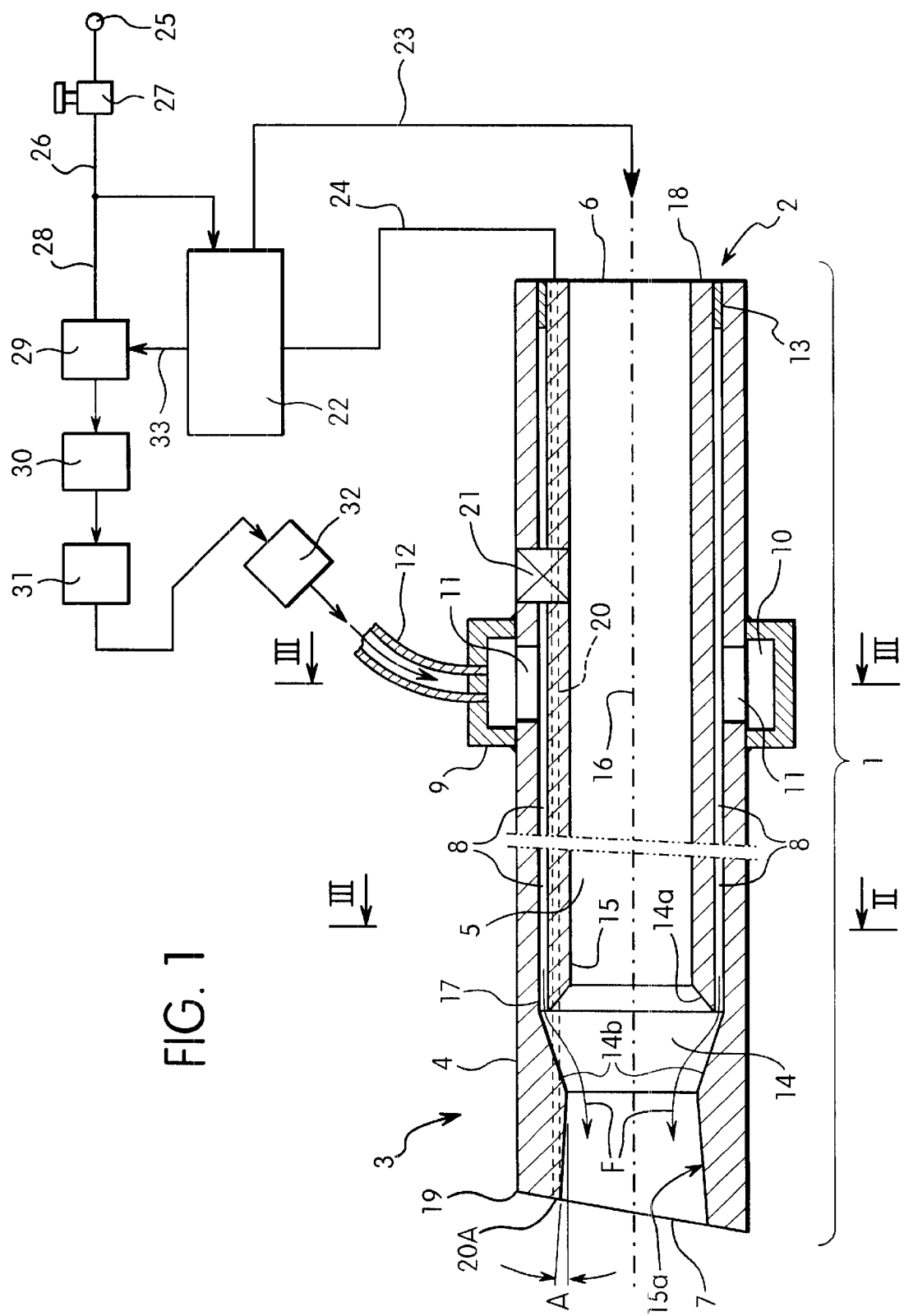
FIG. 1 is a diagrammatic and partial view, in enlarged axial section, of an embodiment of the device of the invention.

FIG. 1 represents, diagrammatically and on a large scale, only the proximal end 2 and distal end 3 of an embodiment 1 of the device according to the invention. This embodiment can constitute, for example, an oronasal endotracheal probe with or without balloon, a pediatric endotracheal probe, a probe for gas monitoring, an endobroncheal probe, a nasopharyngeal probe, an anatomical intubation probe for children, a Cole neonatal probe, a Gedel cannula probe, a nasal probe for oxygen therapy, a nasal or bucconasal mask or a nasal balloon for treatment of sleep apnea.

The device 1 includes a tube 4 which is flexible or pre-shaped (to adapt to the morphology of the patient) and which delimits a main channel 5 opening out via the orifice 6 at the proximal end 2 and via the orifice 7 at the distal end 3.

Thus, the main channel 5 is capable of ensuring passage between the orifices 6 and 7, one of which (orifice 7) is intended to be located within the airways of a patient, while the other (orifice 6) is intended to be located outside said patient. This orifice 6 can open to the ambient air, and in this case the patient can inhale fresh air and exhale vitiated air through the main channel 5. As is explained below, it is also possible to connect the orifice 6 to a source of respirable gas under pressure and to provide a system of unidirectional valves, so that the patient inhales the respirable gas from said source via said main channel 5 and exhales the vitiated gas to the ambient air, again via this main channel.

The diameter of the main channel 5 is of the order of a few millimeters. Satisfactory trials have been conducted with diameters of 3 mm, 7 mm, 8 mm and 12 mm.

Moreover, auxiliary channels 8 are formed within the thickness of the wall of the tube 4, said auxiliary channels 8 extending over almost the entire length of the main channel and being intended to be connected to a source of respirable gas under pressure, as is described below.

The connection to the source of respirable gas under pressure can be effected by means of a ring 9, surrounding the tube 4 in a leaktight manner toward the proximal end 2 and delimiting a sealed annular chamber 10 around said tube. The auxiliary channels 8 are brought into communication with the chamber 10 by means of local cutouts 11 in the wall of the tube 4, and said chamber 10 is connected to said source of respirable gas via a conduit 12. Of course, the proximal ends of the channels 8 are closed, for example by stoppers 13 introduced from the proximal end face 18 of the tube 4.

The auxiliary channels 8 have a smaller diameter than that of the main channel 5. The diameter of the auxiliary channels 8 is preferably less than 1 mm and is advantageously of the order of 400 to 800 microns. At the distal end, the auxiliary channels 8 open into a recess 14 in the inner wall 15 of the tube 4. The recess 14 is annular and centered on the axis 16 of the distal end 3. It includes a face 14a which is substantially transverse or slightly inclined in such a way as to constitute a widening of the main channel 5 into which said auxiliary channels 8 open via their orifices 17, as well as a face 14b following the face 14a and converging in the direction of the axis 16.

Preferably, between the converging inclined face 14b and the distal orifice 7, the inner wall 15 has a part 15a widening slightly outward, as is illustrated by the angle A in FIG. 1.

Thus, when the auxiliary channels 8 are supplied with respirable gas under pressure by way of the elements 9 to 12, the corresponding gaseous jets impact the inclined face 14b, which deflects them in the direction of the axis 16 (arrows F in FIG. 1), generating in the vicinity of the latter a zone of low pressure promoting the gaseous circulation inside the main channel 5, from the proximal orifice toward the distal orifice. This therefore favors the patient's inhalation.

The distance between each of the orifices 17 and the orifice 7 is preferably of the order of 1 to 2 cm.

At least one supplementary channel 20 is provided within the thickness of the tube 4 and opens out at 20A in the vicinity of the distal end 19 of the tube 4 and serves as a pressure tap.

For safety reasons, a calibrated exhaust valve 21 can be provided in the proximal end 2 of the tube 4. Thus, in the event of an accidental overpressure occurring in the main channel 5, gas escapes to outside the patient, via the wall of the tube 4, in order to eliminate this overpressure instantaneously.

Figure 3:
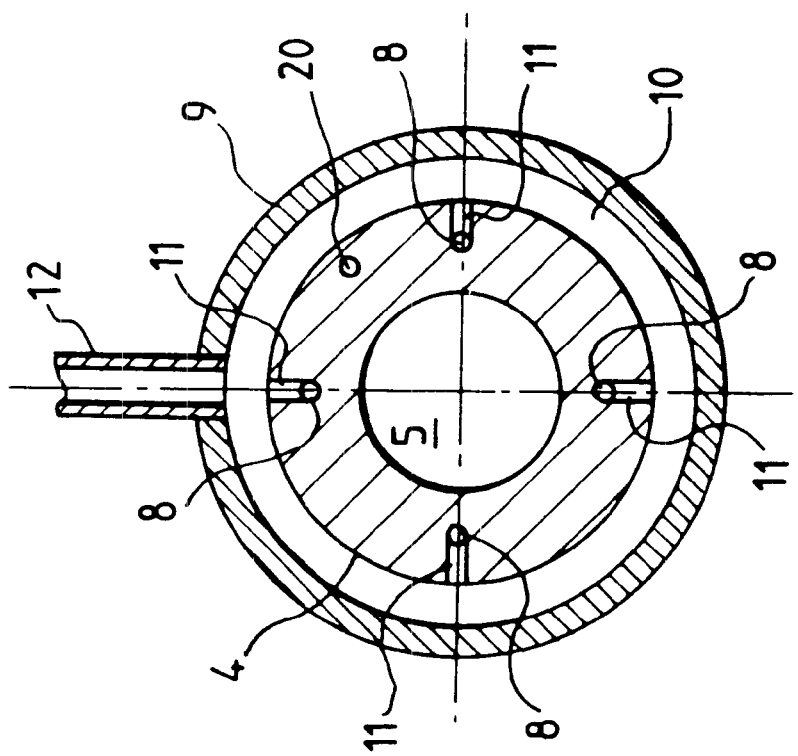
FIGS. 2 and 3 are cross sections along lines II—II and III—III, respectively, in FIG. 1.
Figure 2:
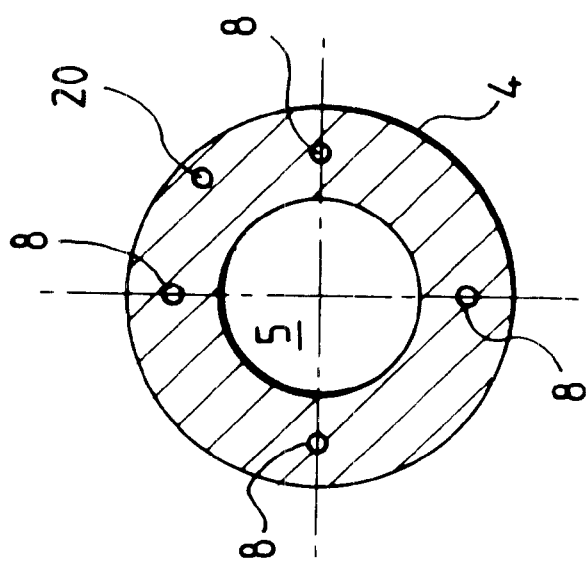

As is shown in FIGS. 2 and 3, the auxiliary channels 8 are arranged regularly around the axis of the tube 4. Their number is variable depending on the applications (adult or child), but is generally between three and nine. Moreover, at least one of the auxiliary channels 8 can be specialized to deliver a medical fluid.

The tube 4 of the device according to the invention can be made of any material already used in respiratory probes, for example polyvinyl chloride, with an optional coating of silicone or steel permitting high-pressure injections.

Of course, the dimensions of the device according to the invention can vary greatly, essentially depending on the mode of fitting of the tube and the size of the patient, who can be an adult, a child, an infant or a premature baby.

The device 1 moreover comprises a supply and control device 22 which is connected to the orifice 6 of the proximal end 2 of the tube 4 via a connection 23 and to the supplementary channel 20 via a connection 24, respectively.

The supply and control device 22 is supplied with respirable gas under pressure via a source 25, to which it is connected via a conduit 26 on which an adjustable pressure reducer/flow meter 27 is mounted.

The outlet of the pressure reducer/flow meter 27 is connected to the conduit 12 via a branch conduit 28 on which there are mounted in series a controllable valve 29, an adjustable device for loss of head 30 for limiting flow rate and pressure, a humidifier 31 and a calibrated exhaust valve 32 of adjustable calibration. The controllable valve 29 is controlled by the supply and control device 22 by way of a connection 33.

By way of nonlimiting example, the pressure reducer/flow meter 27 can deliver the respirable gas coming from the source 25 into the conduit 28 at a pressure P, for example equal to 3.5 bar, with a maximum adjustable flow rate of, for example, 32 liters per minute, while the limiter of flow rate and pressure 30, receiving this respirable gas from the conduit 28, can lower the pressure thereof to a value p which is equal, for example, to 0.5 bar (for an adult) and 0.07 bar (for a child), and can lower the flow rate to a value d which is equal, for example, to 0.5 liter per minute. As for the exhaust valve 32, it is calibrated to the pressure p.

The modes of functioning of the device 1 according to the invention are the following:

in the artificial respiration mode, the supply and control device 22, on the one hand, controls the valve 29 to close by way of the connection 33, so that the conduit 12 is not supplied with gas, and, on the other hand, conveys respirable gas into the tube 4 by way of the connection 23. This device 22 includes means (not shown) by which it is possible to regulate the pressure and flow rate of respirable gas which it receives from the conduit 26 and which it conveys to the tube 4. If an overpressure occurs in the respiratory tract of the patient, it is detected and transmitted, via the supplementary channel 20 and the connection 24, to the device 22 which stops operating. Moreover, if this overpressure exceeds the calibration threshold of the calibrated valve 21—for example because the supplementary channel 20 is obstructed by mucus and has not been able to transmit the overpressure information to the device 22—this valve 21 opens and the proximal channel 5 is connected to the atmosphere;

in the respiratory assistance mode, the supply and control device 22 cuts off the connection 23 in order to bring the orifice 6 into communication with the atmosphere and controls the valve 29 via the connection 33 so that it conveys to the patient a continuous or pulsed jet of respirable gas by way of the limiter 30, the humidifier 31, the calibrated exhaust valve 32 and the auxiliary channels 8. If an overpressure occurs in the respiratory tract of the patient, as was described above, this overpressure is detected and transmitted via the supplementary channel 20, so that the device 22 closes the valve 29 and the conduit 28 stops conveying gas to the patient. If the supplementary channel 20 is obstructed, the device 22 is not warned of the overpressure in the respiratory tract of the patient and cannot stop, but this overpressure causes an increase in pressure in the auxiliary channels 8 and the conduit 12. When this increase in pressure reaches the threshold for opening the safety valve 32, the latter opens and the jet of respirable gas is no longer conveyed to the patient, but on the contrary is diverted to the outside by said safety valve 32. Thus, although in the latter case the safety arrangement 20A, 20, 24, 22, 29 has not been able to function, the jet of respirable gas cannot reach the patient's respiratory system.

Thus, from what has been described above, it will be evident that the invention permits, with maximum safety, humidified respiratory assistance which is nonaggressive with respect to the patient, with almost complete disappearance of the dead space inherent to the known probes.

What is claimed is:

1. A device for respiratory assistance comprising:

a tube which forms a main channel having an axis, a proximal orifice in communication with the ambient atmosphere and a distal orifice intended to be connected to a respiratory tract of a patient, so that said main channel is capable of connecting the respiratory system of said patient to the ambient atmosphere;

at least one auxiliary channel having a proximal end connected to a source of respirable gas via a conduit so as to permit the insufflation of a jet of such a respirable gas into said respiratory system, and a distal end parallel to said main channel and opening through a distal orifice into said main channel in the vicinity of said distal end of said main channel;

surface means disposed opposite of said distal orifice of said auxiliary channel, impacted by said jet of respirable gas and deflecting said jet of respirable gas toward said axis of said main channel, so that the pressure of said jet of respirable gas falls inside said main channel;

a device for loss of head which is external to said tube and is able to limit the flow rate and the pressure of said respirable gas available in said conduit at the outlet of said source, and to impose on said jet of respirable gas a predetermined flow rate value and a predetermined pressure value; and an exhaust valve which is external to said tube and brings said conduit into communication with the ambient atmosphere when the pressure in said conduit exceeds said predetermined pressure value.

2. The device as claimed in claim 1, comprising a humidifier in fluid communication with said conduit connecting said source of respirable gas to said auxiliary channel.

3. The device as claimed in claim 2, wherein said humidifier is arranged between said device for loss of head and said exhaust valve.

* * * * *